(12) United States Patent
Schöllermann, deceased et al.

(10) Patent No.: US 6,181,959 B1
(45) Date of Patent: Jan. 30, 2001

(54) DETECTION OF PARASITIC SIGNALS DURING PULSOXYMETRIC MEASUREMENT

(75) Inventors: Hans Schöllermann, deceased, late of Grenzach-Wyhlen (DE), by Thea Philipp-Schöllermann, legal representative; Patrick Eberhard, Allschwil (CH)

(73) Assignee: Kontron Instruments AG, Schlieren (CH)

( * ) Notice: Under 35 U.S.C. 154(b), the term of this patent shall be extended for 0 days.

(21) Appl. No.: 09/155,586

(22) PCT Filed: Mar. 26, 1997

(86) PCT No.: PCT/CH97/00125

§ 371 Date: Mar. 25, 1999

§ 102(e) Date: Mar. 25, 1999

(87) PCT Pub. No.: WO97/36538

PCT Pub. Date: Oct. 9, 1997

(30) Foreign Application Priority Data

Apr. 1, 1996 (CH) .................................................. 846/96

(51) Int. Cl.⁷ ........................................................ A61B 5/00
(52) U.S. Cl. ............................................................ 600/323
(58) Field of Search ..................... 600/310, 322, 600/323, 330, 336

(56) References Cited

U.S. PATENT DOCUMENTS

| 3,152,587 | 10/1964 | Ullrich et al. . |
| 4,802,486 | 2/1989 | Goodman et al. . |
| 5,025,791 | 6/1991 | Niwa . |
| 5,226,417 | 7/1993 | Swedlow et al. . |
| 5,529,065 | * 6/1996 | Tsuchiya .............................. 600/310 |
| 5,800,349 | * 9/1998 | Isaacson et al. ..................... 600/323 |

FOREIGN PATENT DOCUMENTS

| 3723881 | 1/1989 | (DE) . |
| 9118550 | 12/1991 | (WO) . |
| 9403102 | 2/1994 | (WO) . |

* cited by examiner

Primary Examiner—Eric F. Winakur
(74) Attorney, Agent, or Firm—Selitto & Associates, P.C.

(57) ABSTRACT

In the proposed method for detecting spurious signals caused by movements of the patient or his environment in the pulse oximetric measurement of the arterial oxygen saturation, the intensity of the light emerging from the test specimen is measured by two photodiodes (7, 8). The signals ($S_1$, $S_2$) generated at these photodiodes (7, 8) are normalized to equal levels of their DC components. Finally, to detect spurious signals caused by movements, the differences ($\Delta S_n$) of these normalized signals ($S_{1n}$, $S_{2n}$) are formed.

15 Claims, 2 Drawing Sheets

DETECTION OF PARASITIC SIGNALS DURING PULSOXYMETRIC MEASUREMENT

FIELD OF THE INVENTION

The invention relates to a method for detecting spurious signals caused by movements of a patient or his environment in the pulse oximetric measurement of the arterial oxygen saturation, as well as to a pulse oximeter for carrying out the method.

BACKGROUND OF THE INVENTION

It is known to measure the oxygen saturation of the haemoglobin in the arterial blood (arterial oxygen saturation) by means of a non-invasive method which is designated as pulse oximetry. This method is used for monitoring patients, e.g. during anaesthesia and intensive care. The principle of the measurement is based on the difference between the optical absorbtivities of haemoglobin in its form saturated with oxygen and its reduced form. In the case of red light, the absorption coefficient of blood is greatly dependent upon the oxygen content and, in the case of light in the near infrared range, almost independent thereof. By measuring the ratio of the intensities of the absorbed light of both wavelengths, it is possible to determine the arterial oxygen saturation.

In pulse oximetry, as a rule the light sources employed are two closely mutually adjacent light emitting diodes (LED) having wavelengths of approximately 660 nm (red) and approximately 890 nm (infrared). The light emitted by the two LEDs is passed into a body part (e.g. the pad of the finger) which is well supplied with blood, and is there scattered and partially absorbed. The light emerging is measured by a photodiode which, as a rule, is disposed to be situated opposite the LEDs. The LEDs and the photodiode are usually integrated in an assembly which is designated as a pulse oximetric sensor. The separate measurement of the red and infrared light using only one photodiode is made possible by the use of alternating light pulses of the two wavelengths, which are separately metrologically picked up and evaluated.

The light of both wavelengths which is measured by the photodiode consists of a steady and a time dependent component. The steady component is essentially determined by absorption by bones, tissue, skin and non-pulsating blood. The time dependent component is caused by changes in absorption in the specimen under test, which, in the ideal case, are caused only by the arterial blood flowing in in pulsed fashion. To determine the arterial oxygen saturation ($SaO_2$), the steady components ($DC_R$, $DC_{IR}$) and the time dependent components ($AC_R$, $AC_{IR}$) of the measured red (R) and infrared (IR) light intensities are utilized. Usually, the arterial oxygen saturation is determined using the relation:

$$SaO_2 = f\left(\frac{AC_R}{DC_R} : \frac{AC_{IR}}{DC_{IR}}\right) \quad (1)$$

where f represents an empirically determined function.

A problem which has not yet been satisfactorily solved in pulse oximetric measurement resides in that disturbances to the measurement signals which are caused by movements of the patient or his environment cannot be eliminated entirely. Such disturbances are critical particularly in circumstances in which they occur periodically, since in this case, they may lead under specified conditions to false measurement results. Since the frequency distribution of movement artifacts may overlap that of the physiological signal, conventional band pass filters or selective filters are not suitable for reliably separating movement artifacts from the physiological signal. Even adaptive filter techniques, such as for example the method of adaptive spurious frequency suppression, cannot be directly applied to pulse oximetry, since these presuppose that either the spurious frequencies or the physiological signals exhibit predictable frequency characteristics. This prerequisite is not satisfied either in respect of movement artifacts or in respect of the pulse frequency. In particular in the case of patients having cardiovascular disorders, the latter may exhibit a high variability.

In principle, it has to be stated that, as a consequence of the nature of the problem, limits are set to any solution which is based solely on an improvement of the signal processing. These limits are caused by the fact that disturbances due to movement artifacts cannot be entirely eliminated, since they are not always detected as such. Primarily, it is accordingly necessary to seek a solution via the route of a differentiated signal extraction which permits a separation of the spurious signals from the physiological signals. Various solution routes have already been proposed in this sense.

WO-A-94/03102 contains a description of an optical monitoring device which comprises:

a) a sensor having a transmitter part which has three light emitting diodes which emit light of differing wavelength, and having a receiver part to measure the light intensity, which receiver part has three photodetectors, and b) a control and evaluating part.

To suppress the spurious signals caused by movements of a patient or his environment, it is proposed to normalize the signals generated at the photodetectors to equal levels of their DC components. Proceeding on the basis of the assumption that the amplitudes of the spurious components of these normalized signals are equally large, the differences of the normalized signals are then formed to eliminate the spurious components. However, in practice the amplitudes of the spurious components of the normalized signals are different, as is also mentioned on page 6, lines 4 to 6 of this publication. Accordingly, a complete suppression of spurious signals does not take place.

U.S. Pat. No. 4,802,486 contains a description, for example, of a method which is based on using specified measurement signals, derived from the ECG of the patient, to identify the arterial pulsations. Signals which are not identified as such (i.e. spurious signals) can thus be suppressed. This method, which is designated as ECG-synchronized pulse oximetry, has the disadvantage that spurious signals which occur simultaneously with a pulse signal are not picked up. Moreover, the simultaneous measurement of the ECG is presumed. However, this is not always available.

In U.S. Pat. No. 5,226,417, it is proposed to incorporate into the pulse oximetric sensor a measured value pickup which detects movements at the location of the pulse oximetric test point. Piezoelectric films, acceleration transducers and wire strain gauges are mentioned as examples of such measured value pickups. However, such a solution demands a considerable expenditure in the manufacture of the sensor; this leads to a substantial increase in the cost of the product, which is often designed as a disposable article. Moreover, by reason of the extremely stringent requirements imposed on the sensitivity of the movement detection, a considerable expenditure in respect of signal processing is necessary.

A similar idea is described in U.S. Pat. No. 5,025,791. In that document, it is proposed to incorporate into the pulse oximetric sensor a movement detector which is specifically designed for this purpose and which is based on an electro-mechanical or a magnetic measurement method or a combination of both of these methods. The objections which have already been set forth hereinabove are factors against such a concept.

Another solution is proposed in WO-A-91/18550. That document contains a description of an arrangement which is provided for the measurement of the pulse frequency, the concept of which could however also be transferred to pulse oximetry. In a sensor, which is applied to the forehead of a person, there are incorporated a LED emitting in the infrared and a LED emitting in the yellow frequency range as well as two photodiodes. The light emitted into the tissue of the forehead is back-scattered there and measured by the two photodiodes. The signal generated by the infrared light contains components which are caused both by the pulsating arterial blood and also by movements. In contrast, the signal generated by the yellow light is to a large extent independent of blood pulsations and contains only the components caused by movements. This may be explained in that infra-red light is able to penetrate deeply into the forehead tissue which is well supplied with blood, while yellow light has a substantially smaller depth of penetration and therefore picks up only processes in the vicinity of the surface of the skin of the forehead, i.e. in a region whose blood supply is weak. The two signals can now be analyzed by means of known processes, and the components of the infrared signal which are caused by movements can be removed. In the case of a transfer of this concept to pulse oximetry, it has to be borne in mind that, for reasons which are predominantly practical, but also physiological, the forehead lacks suitability as a test point. The test point which is most frequently used for pulse oximetric measurements is the finger. Measurements are often made also on the ear lobe and on the toe. It is common to these three test points that even the tissue parts which are close to the surface have a good supply of blood. There, a separation of the signal components caused by pulsations and by movements is accordingly not readily possible by the use of light of differing depths of penetration.

OBJECTS OF THE INVENTION

The object of the invention is to provide an improved method for differentiated signal extraction for pulse oximetric measurements, which method permits a detection of the spurious signals caused by movements, and which does not exhibit the disadvantages and limitations of the known methods.

This object is achieved by the method according to the invention for detecting spurious signals, and the pulse oximeter according to the invention for carrying out this method. Preferred variant embodiments are also disclosed.

SUMMARY OF THE INVENTION

According to the invention, the pulse oximetric sensor which is used is a device having a transmitter part which has two light emitting diodes which emit light of differing wavelengths, and having a receiver part to measure light intensity, which receiver part comprises at least two photodiodes. The two or at least two of the photodiodes are, as in the case of the previously known pulse oximetric sensors, disposed opposite the red and infrared LEDs, but offset to different sides with respect to the longitudinal central line of that bearing surface of the receiver part which faces the transmitter part.

An embodiment of such a sensor has the form of a clamp, which is suitable to be secured to a finger. In one of the clamp limbs there are incorporated the red and infrared LEDs, the light of which is emitted into the pad of the finger. Opposite them, in the other limb of the clamp, there are two mutually adjacent photodiodes. The light emitted by the LEDs is scattered in multiple fashion in the pad of the finger, in part absorbed and in part scattered out. A part of the light scattered out passes to the photodiodes. As initially described, the light received by the photodiodes consists of a steady and a time dependent component which is caused by blood pulsations. In the case of movements of the patient or his environment which are transferred to the test point, this causes the addition of a further time dependent component. Accordingly, the signals $S_1$ and $S_2$ measured at the two photodiodes 1 and 2 (light intensities) are made up as follows:

$$S_1 = DC_1 + AC_{P1} + AC_{B1} \qquad (2)$$

$$S_2 = DC_2 + AC_{P2} + AC_{B2}$$

In these expressions, $DC_1$ and $DC_2$ are the steady signal components, i.e. those light intensities which would be measured in the complete absence of blood pulsations and movement artifacts. $AC_{P1}$ and $AC_{P2}$ respectively are the signal components caused by blood pulsations, and $AC_{B1}$ and $AC_{B2}$ respectively are the signal components caused by movements.

In the absence of movement artifacts, the signals $S_1$ and $S_2$ measured at the two photodiodes are very similar. However, in the case of movements very marked differences between them appear. In order to pick up these differences, $S_1$ and $S_2$ are in the first instance normalized to an approximately equal amplitude; expediently, this takes place by means of division by the respective DC values:

$$S_{1n} = \frac{S_1}{DC_1} = 1 + \frac{AC_{P1}}{DC_1} + \frac{AC_{B1}}{DC_1} \qquad (3)$$

$$S_{2n} = \frac{S_2}{DC_2} = 1 + \frac{AC_{P2}}{DC_2} + \frac{AC_{B2}}{DC_2}$$

The thus obtained normalized signals $S_{1n}$ and $S_{2n}$ are subsequently subtracted from one another, and the result is the difference signal $\Delta S_n$:

$$\Delta S_n = S_{1n} - S_{2n} = \left( \frac{AC_{P1}}{DC_1} - \frac{AC_{P2}}{DC_2} \right) + \left( \frac{AC_{B1}}{DC_1} - \frac{AC_{B2}}{DC_2} \right) \qquad (4)$$

or $$\Delta S_n = \Delta S_{nP} + \Delta S_{nB}$$

In these expressions, $\Delta S_{nP}$ are the components of the difference signal caused by pulsations, and $\Delta S_{nB}$ those caused by movements. Measurements which are explicitly described later show that in the absence of movements ($AC_{B1} = AC_{B2} = 0$) the difference signal $\Delta S_n$ determined using red light and also that determined using infrared light is almost equal to zero. This means that the changes in the test specimen which are caused by blood pulsations, at the two adjacent photodiodes, generate almost identical signals. This may be explained in that the red and infrared light is abundantly scattered in the test specimen and, accordingly, the tissue of the pad of the finger is uniformly illuminated. Accordingly, those changes to the optical properties of the test specimen which are caused by blood pulsations act symmetrically on both test points.

In contrast to this, those changes to the optical properties of the test specimen which are caused by movements have different effects. In this case, it is possible to find marked fluctuations of the difference signal $\Delta S_n$ which proceed in a manner temporally synchronous with the movements. Thus, the difference signal $\Delta S_n$ proves to be an extremely sensitive indicator for the detection of movement artifacts of various types, i.e. irrespective of whether these are caused by the patient himself, by external effects on the sensor and the cable, or by other extraneous influences. In particular, it is possible to detect periodically occurring movement artifacts, even when these occur with a frequency which is in the vicinity of the pulse frequency or is even identical therewith. An explanation for this unexpected result must be sought in that movements (in contrast to blood pulsations) result in a non-uniformly distributed change to the optical properties of the test specimen. In the case of movements, the tissue of the pad of the finger is asymmetrically displaced in relation to the positions of the LEDs and the photodiodes; this has the effect of an unequal change to the signals measured at the two adjacent photodiodes.

The advantages attained with the method according to the invention reside in that for the first time a method, which can be realized in technically simple fashion and which is economical, sensitive and reliable, for detecting movement artifacts during pulse oximetric measurements is available. The design of a pulse oximetric sensor having two or more photodiodes differs only in insubstantial fashion from the previously customary designs, since the same optical components are used. It is not necessary to use a separate measured value pickup for the detection of movements, as is proposed in the above cited U.S. Pat. No. 5,226,417 and U.S. Pat. No. 5,025,791. The signal processing is extremely simple and can build on the methods currently used in pulse oximetry. The method can be used at each of the test points which are customary for pulse oximetry. Furthermore, there are no restrictive conditions with respect to the simultaneous availability of a second measurement parameter as in the case of ECG-synchronized pulse oximetry (see U.S. Pat. No. 4,802,486). A further advantage of the method resides in that, with the amplitude of the difference signal $\Delta S_n$, a measure of the magnitude of the spurious signal is available and, accordingly, the disturbance can be quantified in a simple manner.

The detection of movement artifacts with the aid of the method according to the invention makes it possible to take various suitable measures. Thus, with the aid of known methods of analogue or digital electronics, which will not be discussed in greater detail here, the spurious signals determined from the difference signal $\Delta S_n$ can be analyzed, edited and separated from the measured signal. The adjusted physiological signal obtained thereby permits a more precise and more reliable determination of the arterial oxygen saturation. Furthermore, in the case of the occurrence of movement artifacts, an alarm message can be triggered, which causes the user of the pulse oximeter to eliminate the causes of the disturbances. It is also possible to compare the amplitude of the spurious signal with that of the physiological signal and, with effect from a specified ratio of these two values, to trigger an alarm message or no longer to display the measurement result. This may become necessary, for example, in circumstances in which during weak physiological signals, disturbances occur which are so great that the requirements imposed on the accuracy of measurement appertaining to the arterial oxygen saturation can no longer be satisfied.

BRIEF DESCRIPTION OF THE DRAWINGS

In the text which follows, a preferred illustrative embodiment of the invention is described with reference to the accompanying drawings. In the drawings.

DETAILED DESCRIPTION OF THE DRAWINGS

Figure 1B:
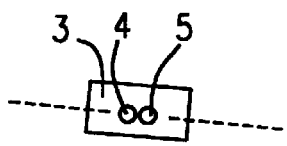
FIGS. 1A–1C show diagrammatic views of a pulse oximetric sensor for measurements on the finger.
Figure 1A:
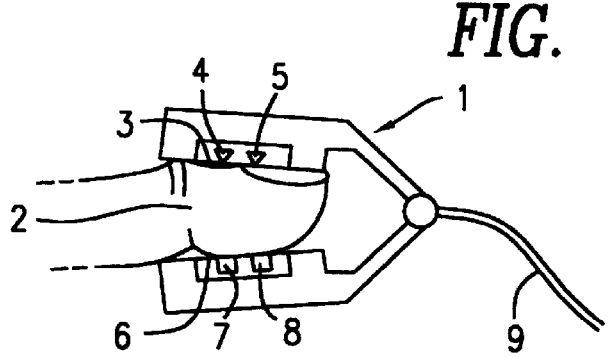
Figure 1C:
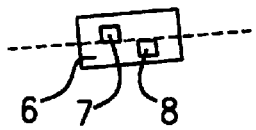

The sensor 1 shown in FIG. 1A has the form of a clamp which is secured to a finger 2. In the bearing surface 3 of the upper limb of the clamp there are a red LED 4 and an infrared LED 5, the light of which is emitted into the pad of the finger. The bearing surface 6 of the opposite limb of the clamp contains two photodiodes 7 and 8 to measure the transmitted light. The four components 4, 5, 7 and 8 are connected via a cable 9 to the control and evaluating part of the pulse oximeter. FIGS. 1B and 1C show in each instance a view of the bearing surfaces 3 and 6, in order to illustrate the positions of the LEDs and of the photodiodes. The LEDs 4 and 5 are incorporated at the smallest possible spacing (approximately 1 to 2 mm) along the central line of the bearing surface 3, which approximately corresponds to the central line of the finger. In contrast, the photodiodes 7 and 8 are disposed to be obliquely offset in relation to the central line of the bearing surface 6. Depending upon their size and the size of the sensor, the spacing between the photodiodes may be approximately 1 to 10 mm. The aim of this geometric arrangement of the photodiodes is the following: as has been described hereinabove, the idea according to the invention resides in detecting those changes to the optical properties of the test specimen which are caused by movements on the basis of their unequal effect on two adjacent test points. Depending upon the nature of the movement, such changes may act more in the direction of the central line of the finger or perpendicular thereto. With the aid of the arrangement of the photodiodes which is offset diagonally to the central line of the finger, it is thus possible to pick up changes in both directions.

It is understood that instead of the clamp-type finger sensor described here, it is also possible to use other types of sensor which are customary in pulse oximetry, e.g. sensors with flexible bearing surfaces. Furthermore, besides the finger, all other body parts which are customarily used for pulse oximetric measurements (e.g. ears, toes) may be used. Furthermore, the concept of the invention is not necessarily restricted to the use of only two photodiodes and to the geometric arrangement which is described here. It is evident that the sensitivity of the detection of movement artifacts can be enhanced by the use of three or more photodiodes; in this case, depending upon the type of sensor, the test point and the number of photodiodes used, the geometric arrangement thereof must be designed in optimal fashion in the individual case.

Figure 2:
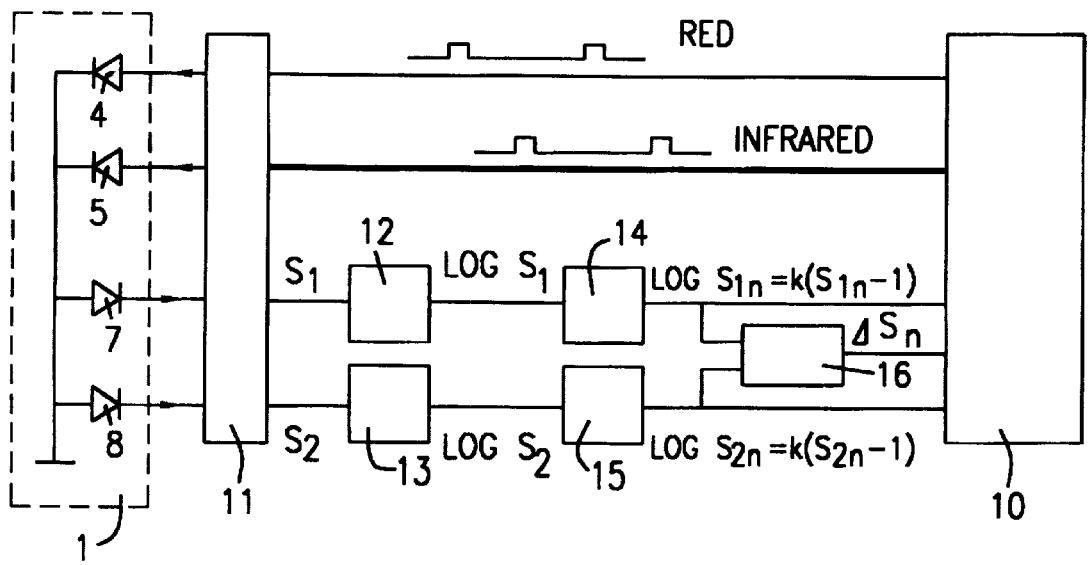
FIG. 2 shows a functional diagram of the circuit parts of a pulse oximeter which are essential to the invention.

FIG. 2 shows a simplified functional diagram of those circuit parts which are necessary for the determination of the difference signal $\Delta S_n$. For the sake of simplicity, all circuit elements which are not directly important to an understanding of the method according to the invention have not been separately shown, but are combined in diagrammatic fashion in the electronic unit 10. The red and infrared LEDs 4 and 5 of the sensor 1 are driven via the electronic unit 10 and the multiplexer 11 in such a way that alternating light pulses of both wavelengths are generated. As has been described hereinabove (see Equation 2), the signals $S_1$ and $S_2$ obtained at the photodiodes 7 and 8 of the sensor 1 consist in each instance of a DC component ($DC_1$, $DC_2$), a first AC component, which is caused by blood pulsations ($AC_{P1}$, $AC_{P2}$), and a second AC component, which is caused by movements ($AC_{B1}$, $AC_{B2}$). Each one of these signals is present both for the red and also for the infrared lights; in this case, however, in the description which follows it is immaterial which one of the two optical wavelengths is used for the determination of $\Delta S_n$. $S_1$ and $S_2$ are in the first instance logarithmized by means of the amplifiers 12 and 13. Subsequently, the DC components of the logarithmized signals are removed by means of the high pass filters 14 and 15. In mathematical terms, the high pass filtering of the logarithmized signal $S_1$ may be described as follows:

$$\log(DC_1 + AC_{PI} + AC_{BI}) - \log DC_1 \qquad (5)$$
$$= \log\left(1 + \frac{AC_{PI}}{DC_1} + \frac{AC_{BI}}{DC_1}\right) = \log S_{1n}$$

$S_{1n}$ is defined by Equation 3. Since, as a rule, the AC components of the signal are substantially smaller than the DC component, i.e., since $$\frac{AC_{PI} + AC_{BI}}{DC_1} \ll 1 \qquad (6)$$

the following relation is approximately applicable:

$$\log S_{1n} = k \cdot \left(\frac{AC_{PI}}{DC_1} + \frac{AC_{BI}}{DC_1}\right) = k \cdot (S_{1n} - 1) \qquad (7)$$

where $k = \log e = 0.434$.

In the case of $S_{2n}$, the following applies in corresponding fashion:

$$\log S_{2n} = k \cdot \left(\frac{AC_{P2}}{DC_2} + \frac{AC_{B2}}{DC_2}\right) = k \cdot (S_{2n} - 1) \qquad (8)$$

The following difference is formed by the amplifier 16:

$$\log S_{1n} - \log S_{2n} = k \Delta S_n \qquad (9)$$

The difference signal $\Delta S_n$ obtained in this way (for definition, see Equation 4) is now available for further processing and evaluation by the electronic unit 10. The methods used in this case will not be discussed in greater detail here, since they do not form part of the subject of the invention.

It is understood that, instead of the circuit concept described here, it is also possible to use other circuits provided that they are suitable for the determination of the normalized difference signal $\Delta S_n$ in accordance with the above definition or a quantity equivalent thereto. Thus, by way of example, it is also possible to use circuits in which, instead of the logarithmization route chosen here, the AC components of the signals $S_1$ and $S_2$ are directly divided by their DC components, and subsequently the difference of the two quotients thus obtained is formed. It is also possible in the first instance to amplify the signals $S_1$ and $S_2$ to equal levels of their DC components and subsequently to form the difference of the signals normalized in this way.

Figure 3:
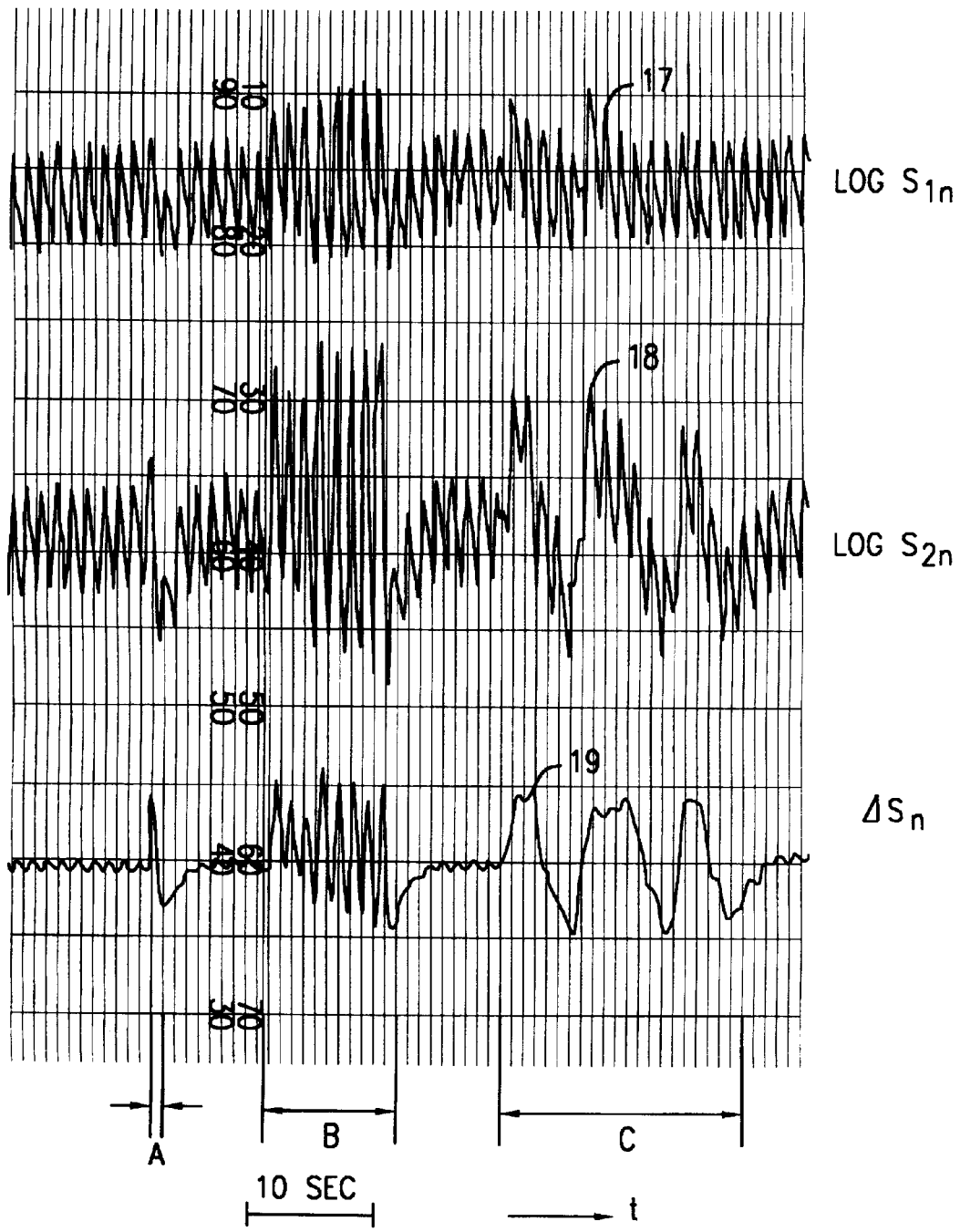
FIG. 3 shows an example of light intensity progressing curves processed in accordance with the invention.

FIG. 3 shows, by way of example, a measurement result which was obtained in the absence and presence of movement artifacts. The upper two curves 17 and 18 show the values, picked off downstream of the high pass filters 14 and 15, of $\log S_{1n} = k(S_{1n}-1)$ and $\log S_{2n} = k(S_{2n}-1)$. The bottom curve 19 shows the signal $\Delta S_n$ obtained downstream of the difference amplifier 16. At the instant A, an individual brief disturbance occurs by reason of a movement of the sensor. During the time intervals B and C periodic disturbances take place, which were caused in each instance by rapid (B) and slow (C) rhythmic movements of the test point (finger). It can be recognized that in the absence of movements $\log S_{1n}$ and $\log S_{2n}$ proceed in very similar fashion and $\Delta S_n$ exhibits only slight, pulse-synchronous fluctuations. As has been mentioned hereinabove, this is to be ascribed to the fact that those signal components of $S_{1n}$ and $S_{2n}$ which are caused by blood pulsations have almost equal amplitudes. In the case of movements, in contrast, it is possible to detect great fluctuations of $\Delta S_n$ which take place in a manner temporally synchronous with the movement sequences. In this case, it should be emphasized that the spurious signals occurring during the time B have approximately the same frequency as the pulse rate and, in this special case, generate for $\log S_{1n}$ and $\log S_{2n}$ curve forms which cannot be distinguished from purely physiological signals. Accordingly, spurious signals of this extreme type cannot be detected using conventional methods of signal analysis. It is a particular advantage of the invention reliably to detect even disturbances of this type.

What is claimed is:

1. A method for detecting spurious signals caused by movements in the pulse oximetric measurement of arterial oxygen saturation, comprising the steps of:
    emitting light into a test specimen;
    measuring the intensity of the light emerging from the test specimen by at least two receptors, each receptor then generating a corresponding signal having a DC component, whereby at least two signals are generated;
    normalizing said at least two signals to equal levels of their DC components, thereby resulting in at least two normalized signals;
    calculating the difference between said at least two normalized signals as a difference signal having an amplitude; and
    analyzing said amplitude of said difference signal to detect spurious signals.

2. The method according to claim 1, wherein the analyzing step includes calculating a ratio of said amplitude of said difference signal to the amplitude of one of said at least two normalized signals, said ratio being used as a measure of the relevance of the spurious signals caused by movements with respect to their influence on the precision of the pulse oximetric measurement of the arterial oxygen saturation.

3. The method according to claims 1 or 2, wherein the normalizing step includes calculating the logarithm of each of said at least two signals and removing the DC component of each logarithmized signal by a high pass filter.

4. A pulse oximeter, comprising:
    a sensor including a transmitter part and a receiver part, said transmitter part having two light emitting diodes which emit light of differing wavelengths, said receiver part having at least two photodiodes which are offset to different sides of said receiver part relative to a longitudinal center line of said receiver part, said at least two photodiodes facing said transmitter part, each of said at least two photodiodes generating a corresponding signal in response to light received, whereby at least two signals are generated; and
    a control and evaluating part which subtracts said at least two signals from one another, to detect spurious signals caused by movement.

5. A pulse oximeter according to claim 4, wherein said sensor is designed in a clamp-type fashion, said transmitter part being disposed on a first limb of said clamp and said receiver part being disposed on a second limb of said clamp.

6. A pulse oximeter according to claim 4, wherein said transmitter part and said receiver part are disposed on a flexible substrate which can be applied to a body part of a patient.

7. A pulse oximeter, comprising:

emitting means for emitting light into a test specimen;

at least two measuring means, each of said at least two measuring means measuring the intensity of the light emerging from the test specimen and generating a signal having a DC component in response to the light, whereby at least two signals are generated;

normalizing means for normalizing said at least two signals to equal levels of their DC components, thereby resulting in at least two normalized signals;

calculating means for calculating the difference between said at least two normalized signals as a difference signal having an amplitude; and analyzing means for analyzing said amplitude of said difference signal to detect spurious signals caused by movement.

8. A pulse oximeter according to claim 7, wherein said emitting means includes two light emitting diodes which emit light of differing wavelengths.

9. A pulse oximeter according to claim 8, wherein one of said light emitting diodes emits red light, and the other of said light emitting diodes emits infrared light.

10. A pulse oximeter according to claim 7, wherein said at least two measuring means includes at least two photodiodes.

11. A pulse oximeter according to claim 7, wherein said normalizing means includes at least two amplifiers, each amplifier receiving a corresponding one of said at least two signals and calculating the logarithm of said corresponding signal, thereby resulting in at least two logarithmized signals; and at least two high pass filters, each high pass filter receiving a corresponding one of said at least two logarithmized signals and removing the DC component of said corresponding logarithmized signal, thereby resulting in said at least two normalized signals.

12. A pulse oximeter according to claim 7, wherein said calculating means includes an amplifier.

13. A method for detecting spurious signals caused by movements in the pulse oximetric measurement of arterial oxygen saturation, comprising the steps of:

emitting light into a test specimen;

measuring the intensity of the light emerging from the test specimen by at least two receptors, each receptor then generating a corresponding signal having a DC component, whereby at least two signals are generated;

normalizing said at least two signals to equal levels of their DC components, thereby resulting in at least two normalized signals, said step of normalizing including calculating the logarithm of each of said at least two signals and removing the DC component of each logarithmized signal by a high pass filter;

calculating the difference between said at least two normalized signals as a difference signal having an amplitude; and analyzing said amplitude of said difference signal to detect spurious signals.

14. The method according to claim 13, wherein the analyzing step includes calculating a ratio of said amplitude of said difference signal to the amplitude of one of said at least two normalized signals, said ratio being used as a measure of the relevance of the spurious signals caused by movements with respect to their influence on the precision of the pulse oximetric measurement of the arterial oxygen saturation.

15. A pulse oximeter, comprising:

emitting means for emitting light into a test specimen;

at least two measuring means, each of said at least two measuring means measuring the intensity of the light emerging from the test specimen and generating a signal having a DC component in response to the light, whereby at least two signals are generated;

normalizing means for normalizing said at least two signals to equal levels of their DC components, said normalizing means including at least two amplifiers, each amplifier receiving a corresponding one of said at least two signals and calculating the logarithm of said corresponding signal, thereby resulting in at least two logarithmized signals, and at least two high pass filters, each high pass filter receiving a corresponding one of said at least two logarithmized signals and removing the DC component of said corresponding logarithmized signal, thereby resulting in at least two normalized signals;

calculating means for calculating the difference between said at least two normalized signals as a difference signal having an amplitude; and analyzing means for analyzing said amplitude of said difference signal to detect spurious signals caused by movement.

* * * * *

UNITED STATES PATENT AND TRADEMARK OFFICE
CERTIFICATE OF CORRECTION

PATENT NO. : 6,181,959 B1
DATED : January 30, 2001
INVENTOR(S) : Hans Schöllerman and Patrick Eberhard It is certified that error appears in the above-identified patent and that said Letters Patent is hereby corrected as shown below:

<u>Title page,</u>
Item [73], should read:
-- [73] Assignee:  Linde Medical Sensors AG, Basel (CH) --

Signed and Sealed this

Twelfth Day of November, 2002

*Attest:*

*Attesting Officer*

JAMES E. ROGAN
*Director of the United States Patent and Trademark Office*